US012806134B2

(12) United States Patent
da Silva et al.

(10) Patent No.: US 12,806,134 B2
(45) Date of Patent: Nov. 24, 2026

(54) ANTIPERSPIRANT COMPOSITION

(71) Applicant: Coty Inc., New York, NY (US)

(72) Inventors: Katia Nunes da Silva, Osasco (BR); Carlos Eduardo Ramos Dalseno, Barueri (BR)

(73) Assignee: Coty Inc., New York, NY (US)

( * ) Notice: Subject to any disclaimer, the term of this patent is extended or adjusted under 35 U.S.C. 154(b) by 43 days.

(21) Appl. No.: 18/565,018

(22) PCT Filed: Jul. 19, 2022

(86) PCT No.: PCT/US2022/073891
§ 371 (c)(1),
(2) Date: Nov. 28, 2023

(87) PCT Pub. No.: WO2023/004315
PCT Pub. Date: Jan. 26, 2023

(65) Prior Publication Data
US 2024/0252424 A1 Aug. 1, 2024

Related U.S. Application Data

(60) Provisional application No. 63/223,449, filed on Jul. 19, 2021.

(51) Int. Cl.
*A61K 8/9789* (2017.01)
*A61K 8/04* (2006.01)
*A61K 8/34* (2006.01)
*A61Q 15/00* (2006.01)

(52) U.S. Cl.
CPC ............ *A61K 8/9789* (2017.08); *A61K 8/046* (2013.01); *A61K 8/345* (2013.01); *A61Q 15/00* (2013.01); *A61K 2800/30* (2013.01)

(58) Field of Classification Search
None
See application file for complete search history.

(56) References Cited

U.S. PATENT DOCUMENTS 3,887,692 A 6/1975 Gilman
3,904,741 A 9/1975 Jones et al.
5,593,663 A 1/1997 Leng et al.
(Continued)

FOREIGN PATENT DOCUMENTS

CN 105708725 A 6/2016
CN 109674693 A 4/2019
(Continued)

OTHER PUBLICATIONS

KR100946584B1—Google English Translation (Year: 2009).*
(Continued)

*Primary Examiner* — Kyung S Chang
(74) *Attorney, Agent, or Firm* — Schwegman Lundberg & Woessner, P.A.

(57) ABSTRACT

The present disclosure provides an antiperspirant composition that includes active component and an inactive component. The antiperspirant composition can be present as a stick antiperspirant, a body spray, a clear gel, or an aerosol antiperspirant. The active component can include a film former and an extract solution. The extract solution can include *Nymphaea coerulea* flower extract and *Nelumbo nucifera* flower extract.

18 Claims, 1 Drawing Sheet

Mean and standard error of sweating for the collection period T2 and time-point T24h

(56) References Cited

U.S. PATENT DOCUMENTS

| | | | |
|---|---|---|---|
| 5,714,137 | A | 2/1998 | Trinh et al. |
| 5,942,217 | A | 8/1999 | Woo et al. |
| 2007/0275866 | A1 | 11/2007 | Dykstra |
| 2010/0047296 | A1 | 2/2010 | Banowski et al. |
| 2012/0237540 | A1 | 9/2012 | Florence et al. |
| 2019/0298625 | A1 | 10/2019 | Hilliard, Jr. et al. |
| 2019/0343731 | A1 | 11/2019 | Amari et al. |

FOREIGN PATENT DOCUMENTS

| | | | |
|---|---|---|---|
| CN | 110585090 | A | 12/2019 |
| CN | 117425470 | | 1/2024 |
| DE | 102007028508 | A1 | 4/2008 |
| GB | 1343653 | A | 1/1974 |
| KR | 100946584 | B1 | 3/2010 |
| KR | 20150097350 | A | 8/2015 |
| WO | WO-2023004315 | A1 | 1/2023 |

OTHER PUBLICATIONS

"International Application Serial No. PCT/US2022/073891, International Search Report mailed Sep. 23, 2022", 2 pgs.

"International Application Serial No. PCT/US2022/073891, Written Opinion mailed Sep. 23, 2022", 7 pgs.

"Chinese Application Serial No. 202280036464.0, Office Action mailed Dec 20, 2025", w/ English Translation, 15 pgs.

"International Application Serial No. PCT US2022 073891, International Preliminary Report on Patentability mailed Feb. 1, 2024", 9 pgs.

"European Application Serial No. 22846793.2, Indication of deficiencies in a request under Rule 22 EPC mailed Feb. 8, 2024", 2 pgs.

"European Application Serial No. 22846793.2, Response filed May 31, 2024 to Indication of deficiencies in a request under Rule 22 EPC mailed Feb. 8, 24", 8 pgs.

"European Application Serial No. 22846793.2, Extended European Search Report mailed Dec. 3, 2024", 9 pgs.

Mintel, "Antiseptic Face and Hair Spray", Database GNPD Mintel anonymous, (Oct. 7, 2020), 3 pgs.

Provital, "Nelupure", XP002810772, [Online] Retrieved from the internet:https: web.archive.org web 20200808033054 https: cosmetics. specialchem.eom product i-provital-nelupure#related-documents, (Aug. 8, 2020), 4 pgs.

* cited by examiner

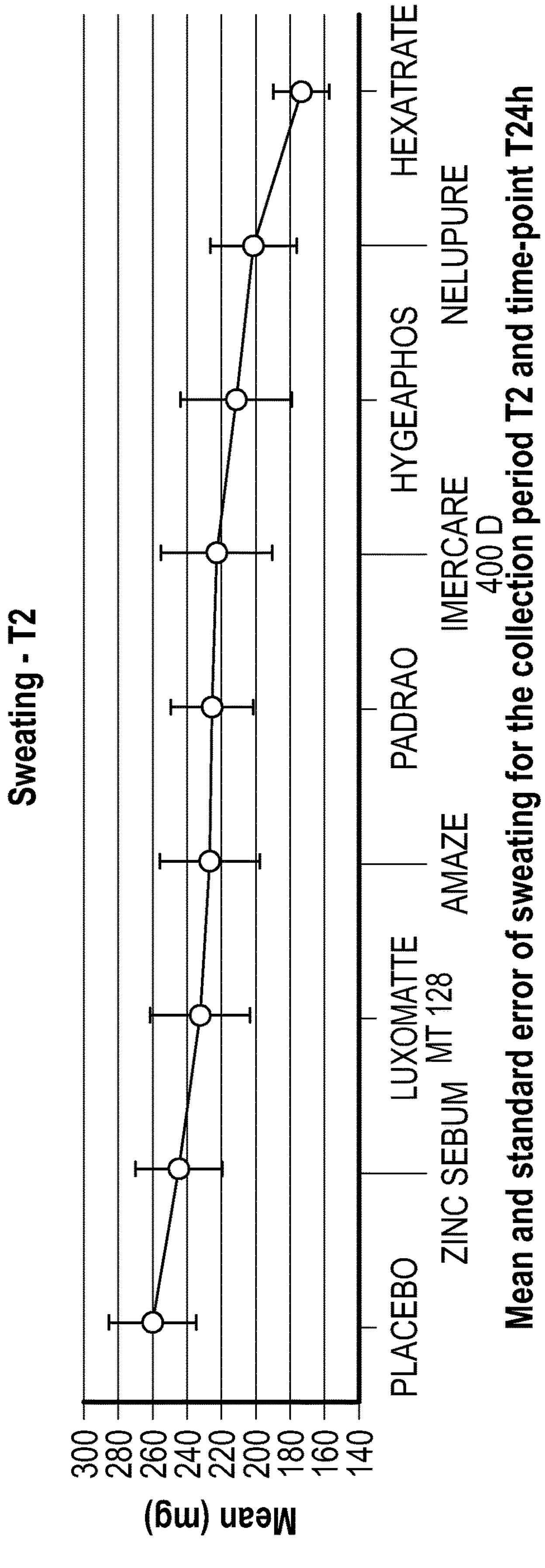
Sweating - T2
Mean (mg)
300
280
260
240
220
200
180
160
140
PLACEBO
ZINC SEBUM
LUXOMATTE MT 128
AMAZE
PADRAO
IMERCARE 400 D
HYGEAPHOS
NELUPURE
HEXATRATE
Mean and standard error of sweating for the collection period T2 and time-point T24h

ANTIPERSPIRANT COMPOSITION

CROSS-REFERENCE TO RELATED APPLICATION

This application is a U.S. National Stage Filing under 35 U.S.C. 371 from International Application No. PCT/US2022/073891, filed on 19 Jul. 2022, and published as WO 2023/004315 on 26 Jan. 2023, which application claims the benefit of priority to U.S. Provisional Patent Application Ser. No. 63/223,449 entitled "ANTIPERSPIRANT COMPOSITION," filed Jul. 19, 2021, the disclosure of which is incorporated herein in its entirety by reference.

BACKGROUND

Consumers desire antiperspirant and deodorant compositions that provide a desired and long-lasting fragrance or scent each time the composition is applied or used. Particularly in the case of deodorants, consumers may also expect compositions that provide a scent that can mask or override other undesirable odors.

SUMMARY OF THE DISCLOSURE

The present disclosure provides an antiperspirant composition that includes active component and an inactive component. The antiperspirant composition can be present as a stick antiperspirant, a body spray, a clear gel, a roll on, a cream, or an aerosol antiperspirant. The active component can include an optional film former, and an extract solution. The extract solution can include *Nymphaea coerulea* flower extract and *Nelumbo nucifera* flower extract. In some aspects, the active component can be free of an aluminum salt.

BRIEF DESCRIPTION OF THE DRAWINGS

FIG. 1 is a graph showing performance of several antiperspirant compositions.

DETAILED DESCRIPTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

According to various aspects of the present disclosure an antiperspirant composition can include an active component and an inactive component. The antiperspirant composition can be present as a stick antiperspirant, a body spray, a clear gel, a roll on, a cream, or an aerosol antiperspirant. The active component can include a film former, and an extract solution. The extract solution can include *Nymphaea coerulea* flower extract and *Nelumbo nucifera* flower extract. The solution is available as a product under the tradename NELUPURE. Without intending to be bound to any theory, it is thought that the extract solution is useful in an antiperspirant composition in part because it reduces the expression of the leptin cellular receptor in sebocytes, thus preventing the triggering of sebum production and inflammatory processes that cause skin blemishes. It has been shown that leptin, a protein synthesized and secreted by different cell types in our body, including skin cells plays a role in the cellular mechanism that triggers sebum synthesis. The benefits of including the extract solution are at least somewhat unexpected because the extract solution may also be an inhibitor of acetylcholinesterase inhibitors.

The ability of the extract solution of *Nymphaea coerulea* flower extract and *Nelumbo nucifera* flower extract to provide beneficial properties as an acetylcholinesterase inhibitors suggests that other natural extracts with acetylcholinesterase inhibition properties can also be used. As a non-limiting list of examples, other natural extracts that can be used alone or in combination include the following species. Where known for each species the portion of the plant and extract solution are specified. Examples of the other natural extract solutions include: *Scadoxus puniceus*, Ethyl acetate extract; *Lannea schweinfurthii*, Ethyl acetate extract (root); *Carpolobia lutea*, Ethyl acetate fraction (root); *Xysmalobium undalatum*, Ethyl acetate extract (root); *Phelegmariurus tetragonus* alkaloidal fraction (aerial parts); *Esenbeckia leiocarpa* (alkaloidal fraction); *Melissa officinalis*.is, Methanolic extract (leaves), *Carpolobia lutea*, Aqueous fraction (root); *Crinum bulbispermum*, Ethyl acetate extract; *Morus alba*, ethyl acetate fraction (root-balk); *Angelica decursiva*, Aqueous fraction (whole plant); *Carpolobia lutea* Methanolic extract (root); *Buchanania axillaris, Methanolic extract; Salvia miltiorrhiza* Bunge Methanolic extract (whole plant); *Huperzia serrata*, Alkaloids fraction (whole plant); *Esenbeckia leiocarpa*. Hexanic fraction (stems); *Berberis aetnensis*, methanolic fraction (root); *Senna obtusifolia*, Ethyl acetate fraction (leaves); *Angelica decursiva* (Miq.), Ethyl acetate fraction (Whole plant); *Senna obtusifolia*, Buthanolic fraction (leaves); *Morus alba*, Methanolic extract (roots); *Zanthoxylum davyi*. Ethyl acetate extract (root); *Morus alba*(Moraoeae), Methanolic extract (root-bark); *Senna obtusifolia*, Chloroform fraction (leaves); *Moros alba*, Chloroform fraction (root-bark); *Senna obtusifolia*, Aqueous fraction (leaves); *Crinum bulbispermum*, Methanolic extract (bulb); *scabiosa arenaria*, Ethyl acetate fraction (stem); *Berberis libanotica*, Methanolic fraction (root); *Pavetta indica*, Methanolic extract (aerial parts); *Crinum jagus*, Alkaloidal fraction (bulb); *Adenia gummifera*, Ethyl acetate extract (root); *huperzia squarrosa*, Ethyl acetate fraction (aerial parts); *Berberis aetnensis*, Alkaloklal fraction (rool); *Ochna obtusata*, Chloroform fraction (aerial parts); *Gossypium herbaceum*, Hydroalcoholic extracts (flowers); *Hippeastrum puniceum*, Alkaloid fraction (bulb); *Hemidesmus indicus*, Chloroform fraction (aerial part); *Scabiosa arenaria*, Buthanolic fraction (stems); *Senna obtusifolia*, Methanolic fraction (leaves); *Morus alba*, Buthanolic fraction (root-bark); *Ficus sur* Forssk., ethylacetate extract (fruit); *Rumex hastatus* Essential Oils (aerial parts); *Acalypha alnifolia*, Chloroform fraction (aerial parts); *Olax nana* Methanolic: extract (leaves); *Nelumbo nucifera*., Buthanolic fraction (leaves); *Persicaria hydropiper*, Hexanic fraction (whole plant); *Berberis aetnensis*, Hexanic fraction (root); *Crinum bulbisperrrum*, Ethyl acetate extract (root); *Huperzia brevifolia*, Alkalodial fraction (aerial parts); Piper capense, Ethyl acetate extract (root); *Searsia mysorensis*, Chloroform fraction (aerial part); *Morus alba*, Aqueous fraction (root-bar!<); *Hemidesmus Indicus*, methanolic extract (aerial part); *Huperzia squarrosa*, Buthanolic fraction (aerial parts); *Esenbeckia leiocarpa* Methanolic extract (stems); *Scabiosa arenaria*, Acetate fraction (flowers); *Pavetta indica*, Chloroform fraction (aerial parts}; *Polygonum hydropiper*, Chloroform fraction (whole plant); *Acalypha alnifolia*, Methanolic extract; *Carpolobia lutea*, Chloroform fraction (leaves); *Pavetta indica*, Buthonolic fraction; *Nelumbo nucifera*, Ethlyacetate fraction (leaves); *Huperzia compacta* Alaloid fraction (aerial parts); *Acalypha alnifolia*, Aqueous fraction (aerial parts); *Nelumbo nucifera*, Chloroform fraction (leaves); *Buchanania axilaris*, Buthanolic fraction (aerial parts); Ramamoorthy, Buthanolic fraction (flowers); *Rumex hastatus*, Chloroform fraction (whole plant); *Scabiosa arenaria*, Methanolic extract (flowers); *Carpolobia lutea*, Ethanolic fraction (leaves); *Ochna obtusata*, Methanolic extract (aerial parts); *Berberis libanotica*, Alkaloidal extract (root); *Searsia mysorensis*, Buthanolic fraction (areal part); *Searsia mysorensis*, Aqueous fraction (aerial part), *Berberis Libanotica*, Hexanic extract (root); *Jatropha gossypifolia*, Ethyl acetate fraction (leaves); *Polygonum hydropiper*, Aqueous fraction (whole plant); *Pavella indica*, Aqueous fraction (aerial parts); *Stemona sessilifolia*, Alkaloidal extracts (root); *Huperzia squarrosa*, Ethanolic extract (aerial parts); *Hemidesmus indicus*, Buthaolic fraction (aerial part); *Rumex hastatus*, Ethyl acetate fraction (whole plant); *Nelumbo nucifera*, Aqueous fraction (leaves); *Persicaria hydropiper*, Essential Oils (leaves); *Hemidesmus indicus*, Aqueous fraction (aerial part); *Buchanania axillaris*, Aqueous fraction (aerial parts); *carpolobia lutea*, Ehanolic extract (stem bark); *Carpolobia lutea*, Hexanic fraction oil (stem); *Carpolobia lutea*, Methanolic fraction (stem); *Elatostema papillosum*, Methanolic extract (leaves); *Scabiosa arenaria*, Aqueous fraction (llowerS); *Ochna obtusata*, Buthanolic fraction (arial parts); *Jatropha gossypifolia* Dichloromethane extract (root); *Nelumbo nucifera*, Methanolic fraction (leaves); *Rumex hastatus*, Methanolic extract (whole plant); *Jatropha gossypifolia*, Methanoic extract (root); *Polygonum hydropiper*, Essential Oils (flowers); *Scabiosa arenaria*, Methanolic extract (stems); *Diplotaxis simplex*, Aqueous extract (seeds); *Persicaria minor*, Aqueous extract (leaves); *Scabiosa arenaria*, Buthanoic fraction (fruhs); *Polygonom hydropiper*, Buthanoic fraction (whole plant); *Huperzia squarrosa*, Hexanic fraction (aerial parts); *Acalypha alnflolia*, Buthanoic fraction; *Atriplex laciniata*, Aqueous fraction (whole plant); *Scabiosa arenaria*, Methanolic extract (fruits); *Atriplex lacinata*, Ethyl acetate fraction (whole plant); *Atriplex lacinata*, Methanolic extract (whole plant); *Jatropha gossypifolla*, dichloromethane extract (leaves); *Justicia adhatoda*, Methanolic extract (leaves); *Polygorom hydropiper*, acetate fraction (whole plant); *Atriplex laciniata*, Hexanic fraction (whole plant); *Diplotaxis harra*, Aqueous extract; *Polygonum minus* Huds., Methanolic extract (whole plant); *Polygonum hydropiper* L, Methanolic extract (leaves); *Ochna obtusata*, Aqueous fraction (aerial parts); *Atriplex laciniata*, Chloroform fraction (whole plant); *Scabiosa arenaria*, Aqueous fraction; *Ochna obtusata* DC, Aqueous extract (flowers); *Polygonum minus* dichloromethane extract (leaves); *Scabiosa arenaria*, Ethyl acetate fraction (fruits); *Polygorom minus*, Aqueous extract (stem); *Salvia leriifolia* Hexane fraction (leaves); *Jacaranda caroba*, Aqueous extract (leaves); *Polygonum minus* Dichloromethane extract (leafs); *Diplotaxis harra*, Aqueous extract (flowers); *Polygonum minus*, Methanolic extract (stem); *Salvia leriifolia*, Dichloromethane fraction (leaves); *Salvia leriifolia*, Ehlyl acetate fraction (leaves); *Rhizophora lamarckii*, Methanol extract (leaves); *Polygonom minus*, Ethanolic extract (leaves); *Jacaranda caroba*, Hydrommethanolic extracts (leaves). A discussion of potentially relevant species can be found in "Naturally Occurring Acetylcholinesterase Inhibitors and Their Potential Use for Alzheimer's Disease Therapy". Coelho, et. Al., Front. Pharmacol., 18 Oct. 2018, Frontiers|Naturally Occurring Acetylcholinesterase Inhibitors and Their Potential Use for Alzheimer's Disease Therapy (frontiersin.org).

In some examples it may be necessary to include the extract solution of *Nymphaea coerulea* flower extract and *Nelumbo nucifera* flower extract along with any of the species mentioned above to provide the beneficial reduction in the expression of the leptin cellular receptor in sebocytes The active component can be free of an aluminum salt in a range of from about 25 wt % to about 55 wt % of the active component, about 35 wt % to about 45 wt % of the active component, less than, equal to, or greater than about 25 wt %, 26, 27, 28, 29, 30, 31, 32, 33, 34, 35, 36, 37, 38, 39, 40, 41, 42, 43, 44, 45, 46, 47, 48, 49, 50, 51, 52, 53, 54, or about 55 wt %. In various further aspects, the active component can be entirely free of an aluminum salt. Examples of aluminum salts that the composition can be free of includes aluminum sesquichlorohydrate. Aluminum salts of this type include aluminum chloride and the aluminum hydroxyhalides having the general formula $Al_2(OH)xQyXH_2O$ where Q is chlorine, bromine or iodine; where x is from about 2 to about 5, and x+y=about 6, and x and y do not need to be integers; and where X is from about 1 to about 6. Aluminum salts of this type can be prepared in the manner described more fully in U.S. Pat. No. 3,887,692 issued to Gilman on Jun. 3, 1975, and U.S. Pat. No. 3,904,741 issued to Jones and Rubino on Sep. 9, 1975.

The zirconium compounds which are useful in the present invention as a salt of the active component include both the zirconium oxy salts and zirconium hydroxyl salts, also referred to as the zirconyl salts and zirconyl hydroxy salts.

When present, the film former can be in a range of from about 1 wt % to 20 wt % of the active component, 2 wt % to about 20 wt % of the active component, about 7 wt % to about 13 wt % of the active component, less than, equal to, or greater than about 2 wt %, 3, 4, 5, 6, 7, 8, 9, 10, 11, 12, 13, 14, 15, 16, 17, 18, 19, or about 20 wt %. As described herein above, the film former can be used to help produce a homogenous mixture of the extract solution as well as help to evenly distribute the antiperspirant composition about a user's skin. According to various aspects, the film former can include Acrylates Copolymer, Acrylates Copolymer (and) Acrylates/Polytrimethylsiloxymethacrylate Copolymer, ACRYLATES/OCTYLACRYLAMIDE COPOLY- MER, Acrylates/C1-2 Succinates/Hydroxyacrylates Copolymer, Acrylates/C12-22 Alkyl Methacrylate Copolymer, Acrylates/Dimethicone Copolymer, Acrylates/Ethylhexyl Acrylate Copolymer, Acrylates/Hydroxyesters Acrylates Copolymer, Acrylates/Lauryl Acrylate/Stearyl Acrylate/Ethylamine Oxide Methacrylate Copolymer, Acrylates/Octylacrylamide Copolymer Acrylates/Polytrimethylsiloxymethacrylate Copolymer, Acrylates/Polytrimethylsiloxymethacrylate Copolymer (and) Laureth-1 Phosphate, Acrylates/t-Butylacrylamide Copolymer, Adipic Acid/Diglycol Crosspolymer, Adipic Acid/Neopentyl Glycol/Trimellitic Anhydride Copolymer, Algin Aluminum Starch OctenylsuccinateAMP-Acrylates Copolymer, Behenyl Methacrylate/t-Butyl Methacrylate Copolymer, *Brassica Campestris/Aleurites Fordi* Oil Copolymer, Butyl Acrylate/Hydroxypropyl Dimethicone Acrylate Copolymer, Butyl Ester of PVM/MA Copolymer, C24-28 Alkyldimethylsiloxy Trimethylsiloxysilicate, Capryloyl Glycerin/Sebacic Acid Copolymer, Diisostearoyl Polyglyceryl-3 Dimer Dilinoleate, Ethyl Ester of PVM/MA Copolymer, Isobutylene/Ethylmaleimide/Hydroxyethylmaleimide Copolymer, Isopropyl Ester of PVM/MA Copolymer, Methacryloyl Ethyl Betaine/Acrylates Copolymer, Octylacrylamide/Acrylates/Butylaminoethyl Methacrylate Copolymer, Phenylpropyldimethylsiloxysilicate, Polyamide-3, Polyamide-8, Polyester-10, Polyester-7, Polyethylene, Polymethylsilsesquioxane, Polyurethane-1, Polyurethane-14 (and) AMP-Acrylates Copolymer, Polyurethane-18, Polyurethane-34, Polyurethane-35, Polyurethane-48, Polyurethane-64, Polyurethane-93, Polyvinyl Stearyl Ether, PPG-17/IPDI/DMPA Copolymer, PPG-26/Dimer Dilinoleate Copolymer, Pullulan, PVP, PVP CROSSPOLYMER, Sodium Polyacrylate, Sodium Polystyrene Sulfonate, Styrene/Acrylates Copolymer, Styrene/VP Copolymer, Triacontanyl PVP, Trifluoropropyldimethylsiloxy/Trimethylsiloxy Silsesquioxane, Trimethylpentanediol/Adipic Acid/Glycerin Crosspolymer, Trimethylsiloxysilicate, VA/Butyl, Maleate/Isobornyl Acrylate Copolymer, VA/Crotonates Copolymer, VA/Crotonates/Vinyl Neodecanoate Copolymer, Vinyl Caprolactam/VP/Dimethylaminoethyl Methacrylate Copolymer, VP/HEXADECENE COPOLYMER, VP/Acrylates/Lauryl Methacrylate Copolymer, VP/Dimethylaminoethylmethacrylate Copolymer, VP/DMAPA Acrylates Copolymer, VP/Eicosene Copolymer, VP/Hexadecene Copolymer, VP/Methacrylamide/Vinyl Imidazole Copolymer, VP/VA Copolymer, VP/Vinyl Caprolactam/DMAPA Acrylates Copolymer, copolymers thereof, or mixtures thereof. In specific aspects, the film former can include sodium polyacrylate.

The extract can be in a range of from about 0.10 wt % to about 5 wt % of the active component, about 0.5 wt % to about 1.5 wt % of the active component, about 0.2 wt % to about 1.0 wt %, less than, equal to, or greater than about 0.5 wt %, 0.6, 0.7, 0.8, 0.9, 1.0, 1.1, 1.2, 1.3, 1.4, or about 1.5 wt %. In addition to the *Nymphaea coerulea* flower extract and *Nelumbo nucifera* flower extract, the extract solution can include additional components. Those additional components can include propanediol and glycerin. In some examples, the *Nymphaea coerulea* flower extract is in a range of from about 0.001 wt % to about 0.01 wt % of the extract, about 0.005 wt % to about 0.009 wt %, less than equal to, or greater than about 0.001 wt %, 0.005, 0.009, or 0.01 wt %. The *Nelumbo nucifera* flower extract can be in a range of from about 0.001 wt % to about 0.01 wt % of the extract, about 0.005 wt % to about 0.009 wt %, less than equal to, or greater than about 0.001 wt %, 0.005, 0.009, or 0.01 wt %. The propanediol can be in a range of from about 0.5 to about 1.5 wt % of the extract, about 0.6 wt % to about 1 wt %, less than, equal to, or greater than about 0.5 wt %, 0.6, 0.7, 0.8, 0.9, 1.0, 1.1, 1.2, 1.3, 1.4, or about 1.5 wt %. The glycerin can be in a range of from about 0.05 wt % to about 0.2 wt % of the extract, about 0.07 wt % to about 0.1 wt %, less than, equal to, or greater than about 0.05 wt %, 0.06, 0.07, 0.08, 0.09, 0.1, or about 0.2 wt %.

The antiperspirant composition can include a solvent. The solvent can be an organic solvent. Where present, the solvent is in a range of from about 10 wt % to about 50 wt % of the active component, about 30 wt % to about 40 wt % of the active component, less than, equal to, or greater than about 30 wt %, 31, 32, 33, 34, 35, 36, 37, 38, 39, 40, 41, 42, 43, 44, 45, 46, 47, 48, 49, or about 50 wt % of the antiperspirant composition. Examples of organic solvents can include an isododecane component, an alkyl benzoate component, and a neopentyl glycol diheptanoate component. Isododecane (an example of which is represented by CAS 31807-55-3) is generally understood to be a clear, colorless and odorless, volatile liquid, which makes it suitable for use in color cosmetics like mascara, eyeliner, lip products, antiperspirant or any product where improved wear properties and no residues are wanted. It does not leave an oily residue. Isododecane is a volatile, lipophilic component for deodorant sprays and hair care applications. It is a hydrocarbon ingredient used as a solvent. The alkyl benzoate component can be C12-15 alkyl benzoate (an example of which is represented by CAS 68411-27-8), which is generally understood to be a low-molecular weight ester of benzoic acid and C12-15 alcohols. C12-15 alkyl benzoate is a clear liquid that is practically odorless. In some examples, the alkyl benzoate component includes a C12 alkyl benzoate, a C13 alkyl benzoate, a C14 alkyl benzoate, a C15 alkyl benzoate, or a mixture thereof. Neopentyl glycol diheptanoate (an example of which is represented by CAS 68855-18-5) is generally understood to be a mixture of texture-enhancing ingredient neopentyl glycol and grape-derived fatty acid heptanoic acid.

According to various aspects of the present disclosure, the antiperspirant composition can include cyclopentasiloxane as a solvent. However, in some aspects, the antiperspirant composition is substantially free of cyclopentasiloxane. For example, the antiperspirant can include less than about 10 wt % cyclopentasiloxane, less than about 9 wt %, less than about 8 wt %, less than about 7 wt %, less than about 6 wt %, less than about 5 wt %, less than about 4 wt %, less than about 3 wt %, less than about 2 wt %, less than about 1 wt %, less than about 0.5 wt %, less than about 0.1 wt %, less than about 0.01 wt %, or less than about 0.001 wt %. in some aspects, the composition is completely free (e.g., includes 0 wt %) of cyclopentasiloxane. The disclosed isododecane component, alkyl benzoate component, and neopentyl glycol diheptanoate component, together, function to effectively replace cyclopentasiloxane in an antiperspirant while yielding an antiperspirant having similar, equal, or superior performance. Replacing cyclopentasiloxane can be desirable because, despite its performance in antiperspirant compositions, regulatory schemes seek to limit cyclopentasiloxane's use in cosmetic products. Therefore, it is important to find an effective substitute for cyclopentasiloxane. The inventors found that the combination of the isododecane component, alkyl benzoate component, and neopentyl glycol diheptanoate component, unexpectantly, provide an adequate replacement for cyclopentasiloxane. For example, an intensity or quantity at least one of spray discharge, amount of residue build-up in an underarm, amount of residue staining of clothing, perceived stickiness, antiperspirant protection, anti-odor protection, softness perception, or a combination thereof of the antiperspirant composition is substantially equal to that of the comparative antiperspirant composition including cyclopentasiloxane.

The antiperspirant composition can include any number of additional components. For example, the antiperspirant composition can include a perfume. The perfume can be in a range of from about 0.001 wt % to about 5 wt % of the antiperspirant composition, about 0.01 wt % to about 0.05 wt %, less than, equal to, or greater than about 0.001 wt %, 0.005, 0.01, 0.05, 0.1, 0.5, 1, 1.5, 2, 2.5, 3, 3.5, 4, 4.5, or about 5 wt %. Perfumes or perfume raw materials can include compounds having a thiol moiety can include 5-methyl-5-sulfanylhexan-3-one; 2-(4-methyl-1-cyclohex-3-enyl)propane-2-thiol; 5-methyl-2-(2-sulfanylpropan-2-yl) cyclohexan-1-one; 4,7,7-trimethyl-6-thiabicyclo[3.2.1]octane; 4-methoxy-2-methylbutane-2-thiol; methanethiol; ethanethiol; prop-2-ene-1-thiol; propane-2-thiol; 2-methylpropane-2-thiol; propane-1-thiol; butane-2-thiol; butane-1-thiol; 2-methylpropane-1-thiol; methyldisulfanylmethane; 2-methylbutane-2-thiol; 3-methylbutane-2-thiol; 3-methylbutane-2-thiol; pentane-2-thiol; pentane-1-thiol; 2-methylbutane-1-thiol; cyclopentanethiol; 3-methyldisulfanylprop-1-ene; methylsulfanyldisulfanylmethane; 1-methyldisulfanylpropane; ethane-1,2-dithiol; 1-(methyldisulfanyl)prop-1-ene; 3-sulfanylbutan-2-one; ethyldisulfanylethane; hexane-1-thiol; 1-ethyldisulfanylpropane; thiophene-2-thiol; propane-1,3-dithiol; 3-sulfanylpentan-2-one; 2-propan-2-yldisulfanylpropane; butane-1,4-dithiol; benzenethiol; ethylsulfanyldisulfanylethane; 3-methylsulfanyldisulfanylprop-1-ene; 1-methylsulfanyldisulfanylpropane; butane-2,3-dithiol; 4-methyl-4-sulfanylpentan-2-one; 3-prop-2-enyldisulfanylprop-1-ene; 1-methoxyhexane-3-thiol; ethyl 2-sulfanylpropanoate; 1-(prop-2-enyldisulfanyl) propane; 1-propyldisulfanylpropane; 1-(4-hydroxy-3-methoxyphenyl)ethanone butane-1,3-dithiol; 1-propyldisulfanylprop-1-ene; 2-methylbenzenethiol; thiophen-2-ylmethanethiol; 3-sulfanylbutan-2-ol; phenylmethanethiol pentane-1,5-dithiol; 2-ethylbenzenethiol; 3-prop-2-enylsulfanyldisulfanylprop-1-ene; methyldisulfanyldisulfanylmethane; 1-propylsulfanyldisulfanylpropane; 2,7,7-trimethylbicyclo[3.1.1]heptane-2-thiol; 2,6-dimethylbenzenethiol; 2-phenylethanethiol; hexane-1,6-dithiol; 2-(methyldisulfanylmethyl)furan; pyridin-2-ylmethanethiol; 2-methoxybenzenethiol; (7,7-dimethyl-2-bicyclo [3.1.1]heptanyl)methanethiol; methyldisulfanylbenzene; 1-butyldisulfanylbutane; (4-methoxyphenyl)methanethiol; 2-sulfanylpropanoic acid; ethyl 2-methyldisulfanylpropanoate; (2E)-3,7-dimethylocta-2,6-diene-1-thiol; 3,7-dimethylocta-2,6-diene-1-thiol; pyrazin-2-ylmethanethiol; methyldisulfanylmethylbenzene; 2-methyl-5-(1-sulfanylpropan-2-yl)cyclohexane-1-thiol; octane-1,8-dithiol; 2-pyrazin-2-ylethanethiol; naphthalene-2-thiol; 2-oxo-3-sulfanylpropanoic acid; 2-thiophen-2-yldisulfanylthiophene; cyclohexyldisulfanylcyclohexane; 2-(furan-2-ylmethyldisulfanylmethyl)furan; phenyldisulfanylbenzene; benzyldisulfanylmethylbenzene; 8-Hydroxy-5-quinolinesulfonic acid; bis(3-methylbutyl) 2-sulfanylbutanedioate; 2-aminoethanesulfonic acid; 2-phenyl-3H-benzimidazole-5-sulfonic acid; and 2-methyl-2-sulfanylpentan-1-ol. The compounds comprising sulfide moiety is selected from the group consisting of 1-butylsulfanylbutane; 2-methylsulfanylpyrazine; 2-methyl-3-methylsulfanylpyrazine; 2-(methylsulfanylmethyl)pyrazine; and mixtures thereof. Non-limiting examples of compounds having a thiazole moiety can include 2-(2-methylpropyl)-1,3-thiazole; 2-(4-methyl-1,3-thiazol-5-yl)ethanol; 4-methyl-2-propan-2-yl-1,3-thiazole; 1-(1,3-thiazol-2-yl)ethanone; 2,4,5-Trimethylthiazole; 2-isopropyl-4-methylthiazole; 4-vinyl-5-methylthiazole; 2,4-Dimethyl-5-acetylthiazole 1,3-thiazole; 4-methyl-1,3-thiazole; 2,4-dimethyl-1,3-thiazole; 4,5-dimethyl-1,3-thiazole; 2,5-dimethyl-1,3-thiazole; 5-ethenyl-4-methyl-1,3-thiazole; 2-ethyl-4-methyl-1,3-thiazole; 4-ethyl-2-methyl-1,3-thiazole; 2-propyl-1,3-thiazole; 2,4,5-trimethyl-1,3-thiazole; 2-ethyl-1,3-thiazole; 2-ethoxy-1,3-thiazole; 2-butan-2-yl-1,3-thiazole; 5-methoxy-2-methyl-1,3-thiazole; 2-ethyl-4,5-dimethyl-1,3-thiazole; 1,3-benzothiazole; 2,5-diethyl-4-methyl-1,3-thiazole; 1-(1,3-thiazol-2-yl)propan-1-one; 4,5-dimethyl-2-(2-methylpropyl)-1,3-thiazole; 2-methyl-1,3-benzothiazole; 1-(2,4-dimethyl-1,3-thiazol-5-yl)ethanone; and 4-methyl-2-propan-2-yl-1,3-thiazole.

Non-limiting examples of further perfumes include compounds having an oxathiane moiety, which can include (2R,4S)-2-methyl-4-propyl-1,3-oxathiane, 2-methyl-4-propyl-1,3-oxathiane, and 2-pentyl-4-propyl-1,3-oxathiane.

Non-limiting examples of further perfumes include compounds containing oxygen, sulfur, and nitrogen include 2-(4-methyl-1,3-thiazol-5-yl)ethanol; 1-(1,3-thiazol-2-yl) ethanone; 6-methyl-7-Oxa-1-thia-4-azaspiro[4.4]nonane; 2-[(furan-2-ylmethyl)sulfanyl]-5-methylpyrazine; 2,4-Dimethyl-5-acetylthiazole; 2-ethoxy-1,3-thiazole; 5-methoxy-2-methyl-1,3-thiazole; 1-(4,5-dihydro-1,3-thiazol-2-yl)ethanone; 1-(1,3-thiazol-2-yl)propan-1-one; 1-(2,4-dimethyl-1,3-thiazol-5-yl)ethanone; 2-amino-4-methylsulfanylbutanoic acid; (2S)-2-amino-4-methylsulfanylbutanoic acid; 8-Hydroxy-5-quinolinesulfonic acid; 2-aminoethanesulfonic acid; 2-phenyl-3H-benzimidazole-5-sulfonic acid.

More specific examples of the thiol moiety can include a-methyl-5-sulfanylhexan-3-one; 2-(4-methyl-1-cyclohex-3-enyl)propane-2-thiol; 5-methyl-2-(2-sulfanylpropan-2-yl) cyclohexan-1-one; 4,7,7-trimethyl-6-thiabicyclo[3.2.1]octane; and 4-methoxy-2-methylbutane-2-thiol.

More specific examples of the sulfide moiety can include 1-butylsulfanylbutane; ethyl 3-methylsulfanylpropanoate; and 2-(methylsulfanylmethyl)furan.

More specific examples of compounds having a thiazole moiety can include 2-(2-methylpropyl)-1,3-thiazole; 2-(4-methyl-1,3-thiazol-5-yl)ethanol; 4-methyl-2-propan-2-yl-1,3-thiazole; 4-methyl-2-propan-2-yl-1,3-thiazole; and 1-(1,3-thiazol-2-yl)ethanone.

A more specific example of compounds having an oxathiane moiety can be (2R,4S)-2-methyl-4-propyl-1,3-oxathiane.

More specific examples of a compound comprising oxygen, sulfur, and nitrogen can include 2-(4-methyl-1,3-thiazol-5-yl)ethanol, 1-(1,3-thiazol-2-yl)ethanone; and 6-methyl-7-Oxa-1-thia-4-azaspiro[4.4]nonane.

In another example, the perfume raw materials can include sulfide moieties or thiazole moieties. The sulfide moieties can include 1-butylsulfanylbutane, 4,7,7-trimethyl-6-thiabicyclo[3.2.1]octane, and 2-methyl-3-methylsulfanylpyrazine. The thiazole moieties can include 1-(1,3-thiazol-2-yl)ethanone.

In another example, the perfume raw materials can be added to a base perfume in a group. Suitable groups can include group (a): 1-butylsulfanylbutane; (2R, 4S)-2-methyl-4-propyl-1,3-oxathiane; and 4-methoxy-2-methylbutane-2-thiol; group (b): 2-(4-methyl-1,3-thiazol-5-yl) ethanol; 7-Oxa-1-thia-4-azaspiro[4.4]nonane; and 6-methyl-, 1-(1,3-thiazol-2-yl) ethanone; group (c): 2-(methylsulfanylmethyl) furan; ethyl 3-methylsulfanylpropanoate; and 1-butylsulfanylbutane; group (d): 5-methyl-5-sulfanylhexan-3-one; 5-methyl-2-(2-sulfanylpropan-2-yl)

cyclohexan-1-one; and 2-(4-methyl-1-cyclohex-3-enyl) propane-2-thiol; group (e): 2-(2-methylpropyl)-1,3-thiazole; 2-(4-methyl-1,3-thiazol-5-yl) ethanol; and 4-methyl-2-propan-2-yl-1,3-thiazole; and group (f): (2R,4S)-2-methyl-4-propyl-1,3-oxathiane; 2-(4-methyl-1-cyclohex-3-enyl) propane-2-thiol; and (NE)-N-[(6E)-2,4,4,7-tetramethylnona-6,8-dien-3-ylidene]hydroxylamine.

Suitable perfume raw materials may be obtained from: Symrise GmbH, with offices located at Muhlenfeldstrasse 1, Holzminden, 37603, Germany; International Flavors & Fragrances Inc., a New York corporation having an address at 521 W 57th Street, New York, NY 10019; Givaudan Suisse SA a Swiss corporation having an address at 1214 Vernier, Switzerland; Firmenich Inc., with offices located at 250 Plainsboro Rd., Plainsboro Township, NJ 08536, United States; and Takasago International Corporation (USA), with offices located at 4 Volvo Drive, Rockleigh, NJ 07647, United States.

Antiperspirants compositions can also incorporate desirable scents through inclusion of perfumes and perfume raw materials in perfume delivery systems. Certain perfume delivery systems, methods of making certain perfume delivery systems, and the uses of such perfume delivery systems are disclosed in U.S. Pre-Grant Publication No. 2007/0275866 A1. The perfumes and perfume raw materials previously disclosed can be used in such perfume delivery systems. Such perfume delivery systems include: polymer-assisted delivery (PAD), molecule-assisted delivery (MAD), fiber-assisted deliver (FAD), amine-assisted delivery (AAD), cyclodextrin delivery system (CD), starch encapsulated accord (SEA), inorganic carrier delivery system (ZIC), and Pro-Perfume (PP). Examples of these perfume delivery systems are further described below.

In some aspects, the antiperspirant composition can include an odor entrapper. Where present, the odor entrapper is present in a range of from about 0.01 wt % to about 5 wt % of the antiperspirant composition, about 0.02 wt % to about 4 wt %, less than, equal to, or greater than about 0.01 wt %, 0.02, 0.05, 0.1, 0.5, 1, 1.5, 2, 2.5, 3, 3.5, 4, 4.5, or about 5 wt %.

Examples of suitable odor entrappers include, for example, solubilized, water-soluble, uncomplexed cyclodextrin. As used herein, the term “cyclodextrin” includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin includes six glucose units, the beta-cyclodextrin includes seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. Cyclodextrin molecules are described in U.S. Pat. Nos. 5,714,137, and 5,942,217. Suitable levels of cyclodextrin are from about 0.1% to about 5%, alternatively from about 0.2% to about 4%, alternatively from about 0.3% to about 3%, alternatively from about 0.4% to about 2%, by weight of the composition.

In some aspects, the antiperspirant composition can further include a buffering agent. Where present, the buffering agent can be in a range of from about 0.001 wt % to about 0.75 wt % of the antiperspirant composition, about 0.01 wt % to about 0.5 wt %, less than, equal to, or greater than about 0.001 wt %, 0.005, 0.01, 0.05, 0.1, 0.5, or about 0.75 wt %.

A buffering agent can be alkaline, acidic or neutral. The buffer can be used in the composition for maintaining the desired pH. The composition may have a pH from about 3 to about 10, from about 4 to about 9, from about 5 to about 8, from about 6 to about 7, or it may have a pH of about 6.5. One unique feature of the polyvinyl amine malodor control polymers is its ability to maintain active nitrogen sites at high pH levels which can help enhance the antibacterial effect which comes, at least in part, from the nitrogen sites. Suitable buffering agents include, for example, hydrochloric acid, sodium hydroxide, potassium hydroxide, and combinations thereof.

In some aspects of the present disclosure, the antiperspirant composition can include a preservative. Where present, the preservative can be a range of from about 0.0001 wt % to about 0.5 wt % of the antiperspirant composition, about 0.0003 wt % to about 0.1 wt %, less than, equal to, or greater than about 0.0001 wt %, 0.0003, 0.0005, 0.001, 0.005, 0.01, 0.05, 0.1, or about 0.5.

When included, the preservative is included in an amount sufficient to prevent spoilage or prevent growth of inadvertently added microorganisms for a specific period of time, but not sufficient enough to contribute to the odor neutralizing performance of the composition. In other words, the preservative is not being used as the antimicrobial compound to kill microorganisms on the surface onto which the composition is deposited in order to eliminate odors produced by microorganisms. Instead, it is being used to prevent spoilage of the composition in order to increase shelf-life.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1, l'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories, Inc.; N,N"-methylenebis {N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hüls America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

The antiperspirant composition can further include an inactive component. The inactive component can be in a range of from about 50 wt % to about 90 wt % of the antiperspirant composition, about 75 wt % to about 85 wt % of the antiperspirant composition, less than, equal to, or greater than about 50 wt %, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or about 90 wt %. when the inactive component is present, the active component is in a range of from about 10 wt % to about 50 wt % of the composition, about 15 wt % to about 25 wt % of the composition, less than, equal to, or greater than about 10 wt %, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 wt % of the antiperspirant composition.

The concentration of the inactive component relative to the active component can impact the antiperspirant's performance. For example, if the inactive component concentration is too large, less perspiration may be blocked or prevented. Additionally, if the antiperspirant composition is an aerosol spray, too much inactive component can lead to blockage of the spray device that the antiperspirant composition is disposed in.

The inactive component can include a propellant. The propellant can be in a range of from about 15 wt % to about 100 wt % of the inactive component, about 80 wt % to about 95 wt % of the active component, less than, equal to, or greater than about 15 wt %, 20, 25, 30, 35, 40, 45, 50, 55, 60, 65, 70, 75, 80, 85, 90, or about 100 wt % of the inactive component. Examples of suitable propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 diflouroethane).

In some examples, the inactive component can include a suspending agent. The suspending agent can be in a range of from about 0.1 wt % to about 5 wt % of the inactive component, about 0.1 wt % to about 2 wt % of the inactive component, less than, equal to, or greater than about 0.1 wt %, 0.5, 1, 1.5, 2, 2.5, 3, 3.5, 4, 4.5, or about 5 wt %. Where present, the suspending agent can include tearalkonium hectorite, which is designed to impart rheological control and suspension and is a suitable thickener for compositions of the present disclosure. It is a highly efficient rheological additive for intermediate to high polarity systems such as cyclomethicones, esters, triglycerides, vegetable oils, alcohols and ketones.

According to various aspects, of the present disclosure the antiperspirant composition can include an antiperspirant concentrate. In some aspects, alcohol is a predominant component of the concentrates provided herein. Useful alcohols include C1-C3 alcohols, with the preferred alcohol being ethanol. In certain examples, the alcohol is employed at a concentration level of from at least about 40%, 50% or 55% to about 80%, by weight of the inactive component.

According to various embodiments of the present disclosure, the antiperspirant composition can be a component of an assembly. For example, if the antiperspirant composition is an aerosol spray, the assembly can include a spray container and the antiperspirant composition. In some further examples, if the antiperspirant composition is a stick, the assembly can include a container with the antiperspirant composition disposed therein.

EXAMPLES

Various embodiments of the present disclosure can be better understood by reference to the following Examples which are offered by way of illustration. The present disclosure is not limited to the Examples given herein.

Tables 1-4 show various formulations of antiperspirant compositions that are within the scope of the present disclosure.

TABLE 1

Formula 1 - Water Base Spray Antiperspirant

| INCI Name | Wt % |
|---|---|
| Butane | 40-60 |
| Aqua | 15-25 |
| Propane | 10-15 |
| Isobutane | 5-10 |
| Isododecane | 2-7 |
| Neopentyl Glycol Diheptanoate | 0.5-3 |
| Dimethicone | 0.2-0.9 |
| PEG/PPG-18/18 Dimethicone | 0.05-0.3 |
| Propanediol | 0.05-0.2 |
| Sodium Benzoate | 0.05-0.2 |
| Triethyl Citrate | 0.05-0.2 |
| Caprylyl Glycol | 0.05-0.2 |
| Ethylhexylglycerin | 0.05-0.2 |
| Glycerin | 0.05-0.2 |
| Nymphaea Coerulea Flower Extract | 0.0005-0.002 |
| Nelumbo Nucifera Flower Extract | 0.0005-0.002 |

TABLE 2

Formula 2 - Roll-on Antiperspirant

| INCI | Wt % |
|---|---|
| Water | 70-90 |
| *Helianthus Annuus* (Sunflower) Seed Oil | 3-6 |
| Glycerin | 3-6 |
| Steareth-2 | 1-5.8 |
| Cetearyl Alcohol | 1-5 |
| Triethyl Citrate | 0.5-4 |
| Xanthan Gum | 0.5-4 |
| Steareth-20 | 0.5-1.5 |
| Ethylhexylglycerin | 0.1-1 |
| Sodium Benzoate | 0.1-1 |
| Chlorphenesin | 0.1-0.3 |
| Propanediol | 0.1-0.3 |
| Disodium EDTA | 0.05-2 |
| Tocopherol | 0.001-0.005 |
| Nymphaea Coerulea Flower Extract | 0.0005-0.003 |
| Nelumbo Nucifera Flower Extract | 0.0005-0.003 |
| Vegetable Oil | 0.0005-0.003 |
| Sodium Hyaluronate | 0.00005-0.0006 |

TABLE 3

| Formula 3 - Hydroalcoholic Formulation | |
|---|---|
| INCI | Wt % |
| Alcohol | 40-60 |
| Water | 25-45 |
| Glycerin | 4-24 |
| 2-Methyl 5-Cyclohexylpentanol | 0.5-1.5 |
| Propanediol | 0.1-1 |
| Nymphaea Coerulea Flower Extract | 0.001-0.01 |
| Nelumbo Nucifera Flower Extract | 0.001-0.01 |

TABLE 4

| Formula 4 - Aqueous Formulaiton | |
|---|---|
| INCI | Wt % |
| Water | 40-60 |
| Glycerin | 4-24 |
| PEG-40 Hydrogenated Castor Oil | 0.1-1 |
| Triethyl Citrate | 0.1-1 |
| Ethylhexylglycerin | 0.1-1 |
| Propanediol | 0.1-1 |
| Nymphaea Coerulea Flower Extract | 0.001-0.01 |
| Nelumbo Nucifera Flower Extract | 0.001-0.01 |

Example 1

A study was conducted to determine the amount of sweat reduction that can be achieved with the compositions. For example the sweat reduction of the composition of Formula 1 was analyzed according to the following protocol.

Procedure to Conduct the Study 1.1. Conditioning Phase

During the conditioning period the participants were instructed to discontinue the use of any products topical at the underarm. Participants were instructed to wash their armpits only with the standard mild soap provided by the laboratory. The conditioning period was 17 days.

1.2. Verification of Aluminum Residue

Participants were instructed to remove their T-shirt and lie on the stretcher with their arms up. The researcher passed cotton-tipped flexible rod across the entire armpit region and then stored it in a properly identified plastic cup. Then, using a disposable pipette, applied the aluminum accusing solution until the tip of the cotton is well watered. If there is aluminum, the added solution will change its color for pink or purple. The procedure was performed before the baseline sauna and before the saunas after 12, 24, 48 and 72 hours of application of the investigational product. All participants were approved in the verification of aluminum residue.

1.3. Underarm Hygiene

Participants were instructed and supervised by the researcher to wash their armpits before applying the investigational product. The armpits were cleaned according to the following procedure, before the baseline sauna and the first application of the investigational product:

a) Wash one of the armpits during the period of 20 seconds with a standard neutral soap;
b) Rinse the armpit under running water until all the soap is completely removed;
c) Dry the armpit with a disposable towel
d) Repeat the same procedure with the other armpit. After cleaning the armpits, the participants received and wore a white tank top, 100% cotton, cleaned with water and mild soap. The armpits were cleaned according to the following procedure, before other applications of the investigational product:
e) Wash one armpit for 10 seconds with a disposable towel saturated with a standard 2% neutral soap solution;
f) Wet a clean disposable towel in running water and rinse the armpit until all soap is completely removed;
g) Gently dry the armpit with a disposable towel; Repeat the same procedure with the other armpit.

1.4. Initial Assessment of Armpits Sweating

Research participants remained in the hot room with a temperature of 37.8±2° C. and relative air humidity=35±5%, for a total period of 80 minutes. To collect sweating were used of absorbents pads, stored in polyethylene containers closed. The pads were placed in the armpits of the participants immediately after they entered the hot room being replaced every 20 minutes. Every 20 minutes of warm up period, the pads were removed and discarded. Then, new pre-weighed pad was placed, being replaced every 20 minutes. The pads relative to the times of 60 to 80 minutes of exposure were removed and weighed, corresponding respectively to T1 and T2. The participants drank 200 mL of water before entering the hot room, and then a further 200 ml of water after spending 40 minutes in the hot room. In the initial assessment the research participants must present at least 100 mg of sweating in each armpit for 20 minutes of heat exposure.

1.5. Application of the Investigational Product

The investigational product was applied for 3 seconds timed, at a distance of 15 cm in a defined armpit area of 24 $cm^2$. The procedure for applying the investigational product was performed four times by the researcher. The investigational product was evenly distributed in the armpits until it completely covered the defined area. After the applications, the participants remained in an air-conditioned place for 30 minutes until the film was completely dried and formed. For each participant one armpit had the product of Formula 1 applied and another armpit had a control.

1.6. Assessment of Underarm Sweat after the Last Application of the Investigational Product After 12, 24, 48 and 72 hours of the last application of the investigational product, the participants were again submitted to the exposure to heat in the hot room. The research participants remained in the sauna with a temperature of 37.8±2° C. and relative humidity=30 to 40%, for a total period of 80 minutes. For the collection of sweating, absorbent pads were used, stored in closed polyethylene packages. The first pads were placed on the participants' armpits immediately after they entered the sauna and they were changed every 20 minutes. After 40 minutes of warm-up, the pads were removed and discarded. Then, new previously weighed pads were placed, being replaced every 20 minutes. The pads for the 60 and 80-minute exposure times were removed and weighed, corresponding to the T3, T4, T5, T6, T7 and T8 times, respectively. The participants ingested 200 ml of water when entering the sauna and 40 minutes after its beginning, in order to maintain the internal level of hydration, allowing a free flow of sweat and evidencing only the effects of the formulation of the tested product. The levels obtained during the first 40 minutes were disregarded. Participants left the sauna, hydrated and waited 5 minutes for restoring and adapting to the outside temperature. Research participants who had less than 100 mg of sweat in the control armpit during 20 minutes of exposure to heat were excluded from the study.

Results 1.6. Initial Assessment of Armpit Sweating

The sweating values obtained in the initial assessment are listed in Appendix V. According to the data obtained, 22 research participants were approved in the initial phase of the study, that is, all had a quantity of sweating equal to or greater than 100 mg per armpit at each time, T1 and T2.

1.7. Assessment of Armpit Sweating after the Last Application of the Investigational Product When in the study there are pre-treatment records (baseline) the ratio of the treated armpit to the control armpit adjusted to the ratio of the right-to-left armpit sweating rate is defined for each individual by the formula:

$$Z=(PC\times T)/(PT\times C)$$

Where: Z is the adjusted ratio, PC is the amount of sweat obtained in the pre-treatment for the control armpit, PT is the amount of sweat obtained in the pre-treatment for the armpit that will receive the treatment, T is the amount of sweat obtained for the armpit treated with the investigational product and C is the amount of sweat obtained for the control armpit.

1.8. Sweat Reduction Percentages

After 12 hours, the percentage of research participants with a sweat reduction greater that 20% was 77.27%. After 24 hours, the percentage of research participants with a sweat reduction greater that 20% was 77.27%. After 48 hours, the percentage of research participants with a sweat reduction greater that 20% was 77.27%. After 72 hours, the percentage of research participants with a sweat reduction greater that 20% was 77.27%.

Example 2: Effectiveness of NELUPURE

FIG. 1 is a graph that shows, the mean and standard deviation with respect to the amount of sweat collected after two hours with various antiperspirant compositions applied to a subject's armpits. As shown in FIG. 1, the composition denoted "NELUPURE". Which, includes an extract that includes *Nymphaea coerulea* flower extract and *Nelumbo nucifera* flower extract shows superior properties in inhibiting perspiration.

The data of FIG. 1 was obtained according to the following procedure:

Conditioning Period

The conditioning period lasted 21 (±4) days. During the first 14(±2) days, the subjects were instructed to use only the standard soap and the standard bacteriostatic deodorant provided by Allergisa, and not to use any other type of product on the underarms. 7±2 days before the start of test product application (14th day of (±2 days) conditioning period), the subjects were instructed to totally interrupt the use of the standard deodorant, not to shave and to keep not using any other product on the axillary area, with the exception of the standard soap.

Distribution of T-Shirts

The T-shirts (100% cotton) used in the test were initially washed with water and neutral soap. Previous to their delivery to the subjects, the T-shirts were again washed only with water. Right after the third application of the product, the subjects received a T-shirt provided by the technician and they were instructed not to take out until the sweating collection and 24 h odor evaluation.

Axillary Sweating Evaluation 24 hours after the 3rd product application, the dry hot room was carried, in which the subjects were submitted to heat exposure for 80 minutes. For the sweating collection, cotton pads were used, previously stored in closed plastic packages. After the initial 40 minutes of the hot room (air conditioning period), the pads were removed from their packaging and placed immediately in the armpits of each subject, being replaced every 20 minutes, corresponding respectively to collection periods T1 and T2. Standardized pads were previously weighed, as well as appropriate clothing during the Hot Room sitting.

Temperature used was 37.8° C.±1° C. and relative humidity between 30% and 40%. Subjects ingested 200 ml of water when starting the Hot Room and also 35 minutes later, in order to maintain the internal level of hydration, allowing the sweat to flow freely and evidencing only the effects of the formulation of the product tested. (FOOD AND DRUG ADMINISTRATION Guidelines for Effectiveness Testing of OTC Antiperspirant Drug Products, 2003).

After the hot room, the pads were weighed again for the subject's sweating quantification.

ADDITIONAL EMBODIMENTS

The following exemplary embodiments are provided, the numbering of which is not to be construed as designating levels of importance:

Aspect 1 provides an antiperspirant composition comprising:

- an active component comprising:
  - an extract solution comprising:
  - *Nymphaea coerulea* flower extract; and
  - *Nelumbo nucifera* flower extract.

Aspect 2 provides the antiperspirant composition of Aspect 1, wherein antiperspirant composition is free of an aluminum salt in a range of from about 25 wt % to about 55 wt % of the active component.

Aspect 3 provides the antiperspirant composition of any one of Aspects 1 or 2, wherein the composition is free of an aluminum salt.

Aspect 4 provides the antiperspirant composition of any one of Aspects 1-3, wherein the composition is free of an aluminum salt that comprises:

- $Al_2(OH)xQyXH_2O$, wherein
- Q is chlorine, bromine or iodine; x is from about 2 to about 5, and x+y=about 6, and x and y do not need to be integers; and where X is from about 1 to about 6.

Aspect 5 provides the antiperspirant composition of any one of Aspects 1-4, wherein the composition is free of an aluminum salt comprising aluminum sesquichlorohydrate.

Aspect 6 provides the antiperspirant composition of any one of Aspects 1-5, wherein the composition further comprises a film former that is in a range of from about 2 wt % to about 20 wt % of the active component.

Aspect 7 provides the antiperspirant composition of Aspects 6, wherein the film former is in a range of from about 7 wt % to about 13 wt % of the active component.

Aspect 8 provides the antiperspirant composition of Aspect 7, wherein the film former comprises Acrylates Copolymer, Acrylates Copolymer (and) Acrylates/Polytrimethylsiloxymethacrylate Copolymer, ACRYLATES/OCTYLACRYLAMIDE COPOLYMER, Acrylates/C1-2 Succinates/Hydroxyacrylates Copolymer, Acrylates/C12-22 Alkyl Methacrylate Copolymer, Acrylates/Dimethicone Copolymer, Acrylates/Ethylhexyl Acrylate Copolymer, Acrylates/Hydroxyesters Acrylates Copolymer, Acrylates/

Lauryl Acrylate/Stearyl Acrylate/Ethylamine Oxide Methacrylate Copolymer, Acrylates/Octylacrylamide Copolymer Acrylates/Polytrimethylsiloxymethacrylate Copolymer, Acrylates/Polytrimethylsiloxymethacrylate Copolymer (and) Laureth-1 Phosphate, Acrylates/t-Butylacrylamide Copolymer, Adipic Acid/Diglycol Crosspolymer, Adipic Acid/Neopentyl Glycol/Trimellitic Anhydride Copolymer, Algin Aluminum Starch OctenylsuccinateAMP-Acrylates Copolymer, Behenyl Methacrylate/t-Butyl Methacrylate Copolymer, *Brassica Campestris/Aleurites Fordi* Oil Copolymer, Butyl Acrylate/Hydroxypropyl Dimethicone Acrylate Copolymer, Butyl Ester of PVM/MA Copolymer, C24-28 Alkyldimethylsiloxy Trimethylsiloxysilicate, Caprylyol Glycerin/Sebacic Acid Copolymer, Diisostearoyl Polyglyceryl-3 Dimer Dilinoleate, Ethyl Ester of PVM/MA Copolymer, Isobutylene/Ethylmaleimide/Hydroxyethylmaleimide Copolymer, Isopropyl Ester of PVM/MA Copolymer, Methacryloyl Ethyl Betaine/Acrylates Copolymer, Octylacrylamide/Acrylates/Butylaminoethyl Methacrylate Copolymer, Phenylpropyldimethylsiloxysilicate, Polyamide-3, Polyamide-8, Polyester-10, Polyester-7, Polyethylene, Polymethylsilsesquioxane, Polyurethane-1, Polyurethane-14 (and) AMP-Acrylates Copolymer, Polyurethane-18, Polyurethane-34, Polyurethane-35, Polyurethane-48, Polyurethane-64, Polyurethane-93, Polyvinyl Stearyl Ether, PPG-17/IPDI/DMPA Copolymer, PPG-26/Dimer Dilinoleate Copolymer, Pullulan, PVP, PVP CROSSPOLYMER, Sodium Polyacrylate, Sodium Polystyrene Sulfonate, Styrene/Acrylates Copolymer, Styrene/VP Copolymer, Triacontanyl PVP, Trifluoropropyldimethylsiloxy/Trimethylsiloxy Silsesquioxane, Trimethylpentanediol/Adipic Acid/Glycerin Crosspolymer, Trimethylsiloxysilicate, VA/Butyl, Maleate/Isobornyl Acrylate Copolymer, VA/Crotonates Copolymer, VA/Crotonates/Vinyl Neodecanoate Copolymer, Vinyl Caprolactam/VP/Dimethylaminoethyl Methacrylate Copolymer, VP/HEXADECENE COPOLYMER, VP/Acrylates/Lauryl Methacrylate Copolymer, VP/Dimethylaminoethylmethacrylate Copolymer, VP/DMAPA Acrylates Copolymer, VP/Eicosene Copolymer, VP/Hexadecene Copolymer, VP/Methacrylamide/Vinyl Imidazole Copolymer, VP/VA Copolymer, VP/Vinyl Caprolactam/DMAPA Acrylates Copolymer, copolymers thereof, or mixtures thereof. In specific aspects, the film former can include sodium polyacrylate.

Aspect 9 provides the antiperspirant composition of Aspect 8, wherein the film former comprises sodium polyacrylate.

Aspect 10 provides the antiperspirant composition of any one of Aspects 1-9, wherein the extract is in a range of from about 0.10 wt % to about 5 wt % of the active component.

Aspect 11 provides the antiperspirant composition of any one of Aspects 1-10, wherein the extract is in a range of from about 0.5 wt % to about 1.5 wt % of the active component.

Aspect 12 provides the antiperspirant composition of any one of Aspects 1-11, wherein the extract further comprises propanediol and glycerin.

Aspect 13 provides the antiperspirant composition of Aspect 12, wherein:

the *Nymphaea coerulea* flower extract is in a range of from about 0.001 to about 0.01 wt % of the extract;

the *Nelumbo nucifera* flower extract is in a range of from about 0.001 to about 0.01 wt % of the extract;

the propanediol is in a range of from about 0.5 to about 1.5 wt % of the extract; and the glycerin is in a range of from about 0.05 wt % to about 0.2 wt % of the extract.

Aspect 14 provides the antiperspirant composition of any one of Aspects 1-13, further comprising a solvent.

Aspect 15 provides the antiperspirant composition of Aspect 14, wherein the solvent comprises an organic solvent.

Aspect 16 provides the antiperspirant composition of any one of Aspects 14 or 15, wherein the solvent is in a range of from about 10 wt % to about 50 wt % of the active component.

Aspect 17 provides the antiperspirant composition of any one of Aspects 14-16, wherein the solvent is in a range of from about 30 wt % to about 40 wt % of the active component.

Aspect 18 provides the antiperspirant composition of any one of Aspects 14-17, wherein the solvent comprises a C12-C15 alkyl benzoate, isododecane, or a mixture thereof.

Aspect 19 provides the antiperspirant composition of Aspect 18, wherein the C12-C15 alkyl benzoate component comprises a C12 alkyl benzoate, a C13 alkyl benzoate, a C14 alkyl benzoate, a C15 alkyl benzoate, or a mixture thereof.

Aspect 20 provides the antiperspirant composition of any one of Aspects 1-19, wherein the antiperspirant composition is a stick antiperspirant, a body spray, a clear gel, or an aerosol antiperspirant.

Aspect 21 provides the antiperspirant composition of any one of Aspects 1-20, further comprising a perfume.

Aspect 22 provides the antiperspirant composition of Aspect 21, wherein the perfume is in a range of from about 0.001 wt % to about 0.1 wt % of the active component.

Aspect 23 provides the antiperspirant composition of any one of Aspects 21 or 22, wherein the perfume is in a range of from about 0.01 wt % to about 0.05 wt % of the active component.

Aspect 24 provides the antiperspirant composition of any one of Aspects 1-23, further comprising a preservative.

Aspect 25 provides the antiperspirant composition of Aspect 24, wherein the preservative is present in a range of from about 0.0001 wt % to about 0.5 wt % of the active component.

Aspect 26 provides the antiperspirant composition of any one of Aspects 24 or 25, wherein the preservative is present in a range of from about 0.0003 wt % to about 0.1 wt % of the active component.

Aspect 27 provides the antiperspirant composition of any one of Aspects 1-26 further comprising an inactive component.

Aspect 28 provides the antiperspirant composition of Aspect 27, wherein the inactive component is in a range of from about 70 wt % to about 90 wt % of the antiperspirant composition.

Aspect 29 provides the antiperspirant composition of any one of Aspects 27 or 28, wherein the inactive component is in a range of from about 75 wt % to about 85 wt % of the antiperspirant composition.

Aspect 30 provides the antiperspirant composition of any one of Aspects 27-29, wherein the active component is in a range of from about 10 wt % to about 30 wt % of the composition.

Aspect 31 provides the antiperspirant composition of any one of Aspects 27-30, wherein the active component is in a range of from about 15 wt % to about 25 wt % of the composition.

Aspect 32 provides the antiperspirant composition of any one of Aspects 27-31, wherein the inactive component comprises a propellant.

Aspect 33 provides the antiperspirant composition of Aspects 32, wherein the propellant is present in a range of from about 15 wt % to about 100 wt % of the inactive component.

Aspect 34 provides the antiperspirant composition of any one of Aspect 32 or 33, wherein the propellant is present in a range of from about 80 wt % to about 95 wt % of the active component.

Aspect 35 provides the antiperspirant composition of any one of Aspects 1-34, wherein the inactive component further comprises a concentrate.

Aspect 36 provides the antiperspirant composition of Aspect 35, wherein the concentrate comprises an alcohol.

Aspect 37 provides the antiperspirant composition of any one of Aspects 1-36, wherein the inactive component further comprises a suspending agent.

Aspect 38 provides the antiperspirant composition of Aspect 37, wherein the suspending agent is in a range of from about 0.1 wt % to about 5 wt % of the inactive component.

Aspect 39 provides the antiperspirant composition of any one of Aspects 37 or 38, wherein the suspending agent is in a range of from about 0.1 wt % to about 2 wt % of the inactive component.

Aspect 40 provides the antiperspirant composition of any one of Aspects 1-xx, wherein the antiperspirant composition is substantially free of cyclopentasiloxane.

Aspect 41 provides an assembly comprising:

a spray container; and the antiperspirant composition of any one of Aspects 1-40. Aspect 42 provides the antiperspirant composition of any one of Aspects 1-41, wherein the antiperspirant composition is capable of reducing perspiration in a subject for a time period in a range of from about 2 hours to about 96 hours.

Aspect 43 provides the antiperspirant composition of any one of Aspects 1-42, wherein the antiperspirant composition is capable of reducing perspiration in a subject for a time period in a range of from about 24 hours to about 48 hours.

Aspect 44 provides the antiperspirant composition of any one of Aspects 1-43, wherein the antiperspirant composition reduces perspiration in a subject relative to a comparative antiperspirant composition that is free of the extract solution comprising *Nymphaea coerulea* and flower extract and *Nelumbo nucifera* flower extract.

Aspect 45 provides a method of using the antiperspirant composition of any one of Aspects 1-44, the method comprising applying the antiperspirant composition to a subject in need thereof for a sufficient time and duration so as to yield at least a 20% in sweat reduction as measured by the procedures of Example 1.

What is claimed is:

1. An antiperspirant composition comprising:

an active component comprising:

an extract solution comprising:

*Nymphaea coerulea* flower extract; and

*Nelumbo nucifera* flower extract; and chlorphenesin in a range of from about 0.1 wt % to about 0.3 wt % of the antiperspirant composition, wherein the antiperspirant composition is free of aluminum salt.

2. The antiperspirant composition of claim 1, wherein the composition further comprises a film former is in a range of from about 2 wt % to about 20 wt % of the active component.

3. The antiperspirant composition of claim 2, wherein the film former comprises Acrylates Copolymer, ACRYLATES/OCTYLACRYLAMIDE COPOLYMER, Acrylates/C 1-2 Succinates/Hydroxyacrylates Copolymer, Acrylates/C 12-22 Alkyl Methacrylate Copolymer, Acrylates/Dimethicone Copolymer, Acrylates/Ethylhexyl Acrylate Copolymer, Acrylates/Hydroxyesters Acrylates Copolymer, Acrylates/Lauryl Acrylate/Stearyl Acrylate/Ethylamine Oxide Methacrylate Copolymer, Acrylates/Octylacrylamide Copolymer, acrylates/polytrimethylsiloxymethacrylate copolymer, Acrylates/t-Butylacrylamide Copolymer, Adipic Acid/Diglycol Crosspolymer, Adipic Acid/Neopentyl Glycol/Trimellitic Anhydride Copolymer, Algin Aluminum Starch OctenylsuccinateAMP-Acrylates Copolymer, Behenyl Methacrylate/t-Butyl Methacrylate Copolymer, *Brassica Campestris/Aleurites* Fordi Oil Copolymer, Butyl Acrylate/Hydroxypropyl Dimethicone Acrylate Copolymer, Butyl Ester of PVM/MA Copolymer, C24-28 Alkyl dimethyl sil oxy Trimethylsiloxysilicate, Caprylоyl Glycerin/Sebacic Acid Copolymer, Diisostearoyl Polyglyceryl-3 Dimer Dilinoleate, Ethyl Ester of PVM/MA Copolymer, Isobutylene/Ethylmaleimide/Hydroxyethylmaleimide Copolymer, Isopropyl Ester of PVM/MA Copolymer, Methacryloyl Ethyl Betaine/Acrylates Copolymer, Octylacrylamide/Acrylates/Butylaminoethyl Methacrylate Copolymer, Phenylpropyldimethylsiloxysilicate, Polyamide-3, Polyamide-8, Polyester-10, Polyester-7, Polyethylene, Polymethylsilsesquioxane, Polyurethane-1, Polyurethane-14 (and) AMP-Acrylates Copolymer, Polyurethane-18, Polyurethane-34, Polyurethane-35, Polyurethane-48, Polyurethane-64, Polyurethane-93, Polyvinyl Stearyl Ether, PPG-17/IPDI/DMPA Copolymer, PPG-26/Dimer Dilinoleate Copolymer, Pullulan, PVP, PVP CROSSPOLYMER, Sodium Polyacrylate, Sodium Polystyrene Sulfonate, Styrene/Acrylates Copolymer, Styrene/VP Copolymer, Triacontanyl PVP, Trifluoropropyldimethylsiloxy/Trimethylsiloxy Silsesquioxane, Trimethylpentanediol/Adipic Acid/Glycerin Crosspolymer, Trimethylsiloxysilicate, VA/Butyl, Maleate/Isobornyl Acrylate Copolymer, VA/Crotonates Copolymer, VA/Crotonates/Vinyl Neodecanoate Copolymer, Vinyl Caprolactam/VP/Dimethylaminoethyl Methacrylate Copolymer, VP/HEXADECENE COPOLYMER, VP/Acrylates/Lauryl Methacrylate Copolymer, VP/Dimethylaminoethylmethacrylate Copolymer, VP/DMAPA Acrylates Copolymer, VP/Eicosene Copolymer, VP/Hexadecene Copolymer, VP/Methacrylamide/Vinyl Imidazole Copolymer, VP/VA Copolymer, VP/Vinyl Caprolactam/DMAPA Acrylates Copolymer, copolymers thereof, or mixtures thereof.

4. The antiperspirant composition of claim 3, wherein the film former comprises sodium polyacrylate.

5. The antiperspirant composition of claim 1, wherein the extract is in a range of from about 0.10 wt % to about 5 wt % of the active component.

6. The antiperspirant composition of claim 1, wherein the extract is in a range of from about 0.5 wt % to about 1.5 wt % of the active component.

7. The antiperspirant composition of claim 1, wherein the extract further comprises propanediol and glycerin.

8. The antiperspirant composition of claim 7, wherein:

the *Nymphaea coerulea* flower extract is in a range of from about 0.001 to about 0.01 wt % of the extract;

the *Nelumbo nucifera* flower extract is in a range of from about 0.001 to about 0.01 wt % of the extract;

the propanediol is in a range of from about 0.5 to about 1.5 wt % of the extract; and the glycerin is in a range of from about 0.05 wt % to about 0.2 wt % of the extract.

9. The antiperspirant composition of claim 1, further comprising an inactive component.

10. The antiperspirant composition of claim 1, wherein the active component is in a range of from about 10 wt % to about 30 wt % of the composition.

11. The antiperspirant composition of claim 10, wherein the inactive component comprises a propellant.

12. An antiperspirant composition comprising:

an active component comprising:

an extract solution comprising:

*Nymphaea coerulea* flower extract; and

*Nelumbo nucifera* flower extract; and a propellant component comprising:

propane; and isobutane;

wherein the antiperspirant composition is free of aluminum salt.

13. The antiperspirant composition of claim 12, wherein the antiperspirant composition is capable of reducing perspiration in a subject for a time period in a range of from about 2 hours to about 96 hours.

14. The antiperspirant composition of claim 13, wherein the antiperspirant composition is capable of reducing perspiration in a subject for a time period in a range of from about 24 hours to about 48 hours.

15. The antiperspirant composition of claim 14, wherein the antiperspirant composition reduces perspiration in a subject relative to a comparative antiperspirant composition that is free of the extract solution comprising *Nymphaea coerulea* and flower extract and *Nelumbo nucifera* flower extract.

16. The antiperspirant composition of claim 12, wherein the extract is in a range of from about 0.5 wt % to about 1.5 wt % of the active component.

17. The antiperspirant composition of claim 12, wherein:

propane is in a range of from about 10 wt % to about 15 wt % of the antiperspirant composition; and isobutane is in a range of from about 5 wt % to about 10 wt % of the antiperspirant composition.

18. An antiperspirant composition comprising:

an active component comprising:

an extract solution comprising:

*Nymphaea coerulea* flower extract; and

*Nelumbo nucifera* flower extract; and 2-methyl-5-cyclohexylpentanol in a range of from about 0.5 wt % to about 1.5 wt % of the antiperspirant composition, wherein the antiperspirant composition is free of aluminum salt.

* * * * *